US010143395B2

(12) United States Patent
Chakravarthy et al.

(10) Patent No.: US 10,143,395 B2
(45) Date of Patent: Dec. 4, 2018

(54) SYSTEM AND METHOD FOR CARDIAC MONITORING USING RATE-BASED SENSITIVITY LEVELS (71) Applicant: Medtronic Monitoring, Inc., San Jose, CA (US)

(72) Inventors: Niranjan Chakravarthy, Eden Prairie, MN (US); Rodolphe Katra, Blaine, MN (US)

(73) Assignee: MEDTRONIC MONITORING, INC., San Jose, CA (US)

( * ) Notice: Subject to any disclaimer, the term of this patent is extended or adjusted under 35 U.S.C. 154(b) by 141 days.

(21) Appl. No.: 15/278,566

(22) Filed: Sep. 28, 2016

(65) Prior Publication Data
US 2018/0085021 A1 Mar. 29, 2018

(51) Int. Cl.
A61B 5/04 (2006.01)
A61B 5/0464 (2006.01)
(Continued)

(52) U.S. Cl.
CPC .......... *A61B 5/0464* (2013.01); *A61B 5/0006* (2013.01); *A61B 5/0022* (2013.01); *A61B 5/0245* (2013.01); *A61B 5/02405* (2013.01); *A61B 5/02455* (2013.01); *A61B 5/046* (2013.01); *A61B 5/04017* (2013.01); *A61B 5/0422* (2013.01); *A61B 5/0432* (2013.01);
(Continued)

(58) Field of Classification Search
CPC ..... A61B 5/0464; A61B 5/7264; A61B 5/686; A61B 5/7275; A61B 5/0031; A61B 5/0022; A61B 5/04012; A61B 5/7225; A61B 5/6867; A61B 2560/0468; A61B 2560/0481; A61B 2505/07
USPC ........................................................ 600/518
See application file for complete search history.

(56) References Cited

U.S. PATENT DOCUMENTS 4,830,006 A   5/1989   Haluska et al.
4,940,054 A   7/1990   Grevis
(Continued)

FOREIGN PATENT DOCUMENTS

EP   1114653 A2   7/2001
EP   2777494 A1   9/2014
(Continued)

OTHER PUBLICATIONS

"Search Report and Written Opinion for PCT/US2017/053635 dated Jan. 24, 2018".
(Continued)

Primary Examiner — Amanda Hulbert
Assistant Examiner — Roland Dinga
(74) Attorney, Agent, or Firm — Billion & Armitage; Michael A. Collins (57) ABSTRACT A system and method for detecting arrhythmic electrocardiogram (ECG) signals includes defining a plurality of threshold heart rates and rate-dependent sensitivity levels for detecting arrhythmic ECG episodes, wherein more clinically relevant heart rates are assigned rate-dependent sensitivity levels with higher sensitivities. ECG signals are monitored by a medical device, and monitored ECG signals are processed using the plurality of threshold heart rates and rate-dependent sensitivity levels to detect and capture arrhythmic ECG segments.

17 Claims, 7 Drawing Sheets (51) Int. Cl.
| | |
|---|---|
| *A61B 5/00* | (2006.01) |
| *A61B 5/024* | (2006.01) |
| *A61B 5/0245* | (2006.01) |
| *A61B 5/0408* | (2006.01) |
| *A61B 5/042* | (2006.01) |
| *A61B 5/0432* | (2006.01) |
| *A61B 5/11* | (2006.01) |
| *A61B 5/046* | (2006.01) |
| *G06F 19/00* | (2018.01) |
| *G16H 40/67* | (2018.01) |
| *A61B 5/0456* | (2006.01) |

(52) U.S. Cl.
CPC ........ *A61B 5/04087* (2013.01); *A61B 5/1118* (2013.01); *A61B 5/1123* (2013.01); *G06F 19/00* (2013.01); *G16H 40/67* (2018.01); *A61B 5/0456* (2013.01); *A61B 5/7264* (2013.01); *A61B 2505/07* (2013.01)

(56) References Cited

U.S. PATENT DOCUMENTS

| | | | |
|---|---|---|---|
| 5,607,460 | A | 3/1997 | Kroll et al. |
| 6,625,490 | B1 | 9/2003 | McClure |
| 6,922,584 | B2 | 7/2005 | Wang et al. |
| 7,031,765 | B2 | 4/2006 | Ritcher et al. |
| 7,280,869 | B2 | 10/2007 | Warman et al. |
| 7,447,544 | B1 | 11/2008 | Kroll |
| 7,634,310 | B2 | 12/2009 | Lee et al. |
| 8,175,708 | B1 | 5/2012 | Snell et al. |
| 8,326,407 | B2 | 12/2012 | Linker |
| 8,694,098 | B2 | 4/2014 | Vincent et al. |
| 8,790,259 | B2 | 7/2014 | Katra et al. |
| 8,897,863 | B2 | 11/2014 | Linker |
| 8,965,498 | B2 | 2/2015 | Katra et al. |
| 9,173,615 | B2 | 11/2015 | Katra et al. |
| 9,314,178 | B2 | 4/2016 | Katra et al. |
| 2007/0213599 | A1 | 9/2007 | Siejko et al. |
| 2008/0051843 | A1 | 2/2008 | Li et al. |
| 2009/0287268 | A1 | 11/2009 | Nabutovsky et al. |
| 2011/0257535 | A1* | 10/2011 | Michelson ......... A61B 5/02405 600/484 |
| 2012/0101392 | A1 | 4/2012 | Bhunia et al. |
| 2013/0274584 | A1 | 10/2013 | Finlay et al. |
| 2014/0371604 | A1 | 12/2014 | Katra et al. |
| 2015/0088216 | A1 | 3/2015 | Gordon et al. |
| 2015/0126822 | A1 | 5/2015 | Chavan et al. |
| 2016/0045131 | A1 | 2/2016 | Siejko |
| 2016/0135708 | A1 | 5/2016 | Chakravarthy et al. |

FOREIGN PATENT DOCUMENTS

| | | |
|---|---|---|
| WO | 2015066430 A1 | 5/2015 |
| WO | 2016007657 A1 | 1/2016 |

OTHER PUBLICATIONS

"Search Report and Written Opinion for PCT/US2017/053651 dated Dec. 4, 2017".

Garcia, et al., "Arrhythmia Recognition, The Art of Interpretation", Jones & Bartlett Learning, First Edition, Nov. 12, 2003, 392-393, 534-535.

"Tachycardia With a Pulse Algorithm", ACLS Training Center.

* cited by examiner

| Triggering Heart-Rate Threshold | Rate-Based Sensitivity Level | Ratio of Beats Exceeding Threshold | Trigger Condition | Activity Level | Captured ECG Segment |
|---|---|---|---|---|---|
| 130 BPM | Low Sensitivity (e.g., 15 beats out of 20) | 17 beats out of 20 | Tachycardia | At Rest | First ECG Segment |
| 130 BPM | Low Sensitivity (e.g., 15 beats out of 20) | 15 beats out of 20 | Tachycardia | Active | Second ECG Segment |
| 180 BPM | Low Sensitivity (e.g., 5 beats out of 20) | 15 beats out of 20 | Tachycardia | At Rest | Third ECG Segment |
| 180 BPM | Low Sensitivity (e.g., 5 beats out of 20) | 5 beats out of 20 | Tachycardia | Active | Third ECG Segment |
| 30 BPM | Low Sensitivity (e.g., 2 beats out of 5) | 5 beats out of 5 | Bradycardia | At Rest | Fourth ECG Segment |
| 40 BPM | Low Sensitivity (e.g., 3 beats out of 5) | 4 beats out of 5 | Bradycardia | At Rest | Fifth ECG Segment |
| 50 BPM | Low Sensitivity (e.g., 5 beats out of 5) | 5 beats out of 5 | Bradycardia | At Rest | Sixth ECG Segment |

SYSTEM AND METHOD FOR CARDIAC MONITORING USING RATE-BASED SENSITIVITY LEVELS

TECHNICAL FIELD

The present disclosure is related in general to patient monitoring and in particular to detecting cardiac rhythm disorders.

BACKGROUND

Cardiac monitoring—particularly ambulatory monitoring—includes long-term monitoring of ECG signals to detect various type of heart rhythm disorders. The amount of ECG data collected, however, precludes human operator/technician review of the data. Automatic processing of the collected ECG data is utilized to detect and capture ECG segments corresponding with detected heart rhythm disorders. However, while some of the ECG segments captured correspond with an actual heart rhythm disorders (i.e., a true positive event), other ECG segments were incorrectly identified as corresponding to a heart rhythm disorder (i.e., a false positive event). In addition, each captured ECG segment identified as corresponding to a heart rhythm disorder and captured represents a cost. That cost includes the cost of storing the captured ECG segment either on the monitoring device or externally, the cost of power required to communicate the captured ECG segment from the monitoring device to a remote monitoring center, and time required for a HCP to review the captured ECG episode and determine whether action is required. Thus, it is beneficial to reduce the ECG segments incorrectly identified as corresponding to a heart rhythm disorder (i.e., minimize false positive events). However, it is also important to ensure that heart rhythm disorders are detected and corresponding ECG segments captured and provided to a human HCP for review (i.e., avoid missing detection of positive events, or false negative).

It would therefore be beneficial to provide a monitoring system that balances these concerns to ensure clinically relevant ECG segments are captured while maintaining a low-cost system.

BRIEF SUMMARY OF THE INVENTION

According to an exemplary embodiment, a method of detecting arrhythmic electrocardiogram (ECG) segments comprises defining a plurality of threshold heart rates and rate-dependent sensitivity levels for detecting arrhythmic ECG episodes, wherein more clinically relevant heart rates are assigned rate-dependent sensitivity levels with higher sensitivities. ECG signals associated with a patient are monitored using a monitoring device and the monitored ECG signals are processed using the plurality of threshold heart rates and rate-dependent sensitivity levels to detect and capture arrhythmic ECG segments.

According to another exemplary embodiment, a system for monitoring electrocardiogram (ECG) signals and detecting arrhythmic ECG episodes comprises a monitoring device and a processing module. The monitoring device includes one or more electrodes and sensing circuitry for monitoring ECG signals associated with a patient. The processing module is configured to receive the monitored ECG signal, and to utilize the plurality of heart-rate thresholds and rate-dependent sensitivity levels to detect and capture arrhythmic ECG segments.

According to another exemplary embodiment, a medical device comprises a sensing unit, a memory unit, and a processor. The sensing unit is capable of monitoring an electrocardiogram (ECG) signal of the patient. The memory unit stores a plurality of heart-rate thresholds and rate-dependent sensitivity levels, and the processor processes the monitored ECG signal to detect and capture arrhythmic ECG segments based on the plurality of heart-rate thresholds and rate-dependent sensitivity levels.

DETAILED DESCRIPTION

The present invention provides a system and method of monitoring and processing electrocardiogram (ECG) signals to automatically capture clinically relevant ECG segments for subsequent review. In particular, rate-dependent sensitivity/specificity levels are assigned based on the clinical relevance of the underlying cardiac abnormality, with the rate-dependent sensitivity assigned a higher level for more clinically relevant cardiac conditions such as high-rate tachycardia or low-rate bradycardia. In some embodiments, the rate-based sensitivity/specificity levels utilized by the monitoring device are based on one or more patient characteristics, such as age, basal/resting heart rate, etc. In addition, in some embodiments the sensitivity/specificity profiles are programmable by a health care professional (HCP)—either at the onset of the prescribed monitoring period or during the monitoring period in response to the diagnostic yield of the monitoring device.

The terms "sensitivity" and "specificity" are used throughout this disclosure. In general, sensitivity is a measure of the proportion of positive events that are correctly identified as such, otherwise referred to as the true positive rate. Specificity is the reciprocal of sensitivity and is a measure of the proportion of negative events that are correctly identified as such, otherwise referred to as the true negative rate. In this way, sensitivity quantifies the avoiding of false negatives while specificity quantifies the avoiding of false positives. Utilizing a higher sensitivity level reduces the risk of missing a true positive event (e.g., arrhythmia), but at a cost of identifying more false positive events (i.e., low specificity, normal sinus rhythm incorrectly identified as arrhythmic). Conversely, utilizing a high specificity reduces the number of false positive events (i.e., ECG segments incorrectly identified as arrhythmic), but at a cost of potentially failing to identify a true positive event (e.g., arrhythmia). Because sensitivity and specificity are reciprocal in nature, most embodiments are described with respect to a rate-based sensitivity level, but it should be understood that a rate-based specificity level may similarly be utilized.

In one embodiment, monitoring devices detect a positive event (e.g., tachycardia, bradycardia, etc.) when the monitored heart rate in X out of the last Y beats (e.g., 13 out of the last 19 beats) exceeds a heart rate threshold (e.g., 130 BPM, 150 BPM, 165 BPM, or 180 BPM). The value of the variables X and Y in this case determine the sensitivity level, and can be modified either alone or in combination to increase or decrease the sensitivity. The sensitivity can be increased by utilizing a smaller ratio of X to Y, and is decreased by increasing the ratio of X to Y. For example, setting X equal to 10 and Y equal to 20 requires that 10 beats out of 20 must exceed the heart rate threshold to trigger capture of the ECG segment. The sensitivity level is increased if X is set equal to 5 and Y remains equal to 20, such that only 5 beats out of 20 must exceed the heart rate threshold to trigger capture of the ECG segment—and is therefore more sensitive. Likewise, the sensitivity level is decreased if X is set equal to 15 and Y is set equal to 18, such that now 15 beats out of 18 must exceed the heart rate threshold to trigger capture of the ECG segment. Specificity may also be defined in terms of the variables X and Y, but whereas sensitivity is increased by lowering the value of the ratio X/Y, specificity is increased by increasing the value of the ratio X/Y. For the sake of simplicity, the present disclosure describes the sensitivity/specificity in terms of level (e.g., high, medium, low) rather than in terms of the value of X/Y utilized to determine the desired sensitivity/specificity level.

Figure 1:
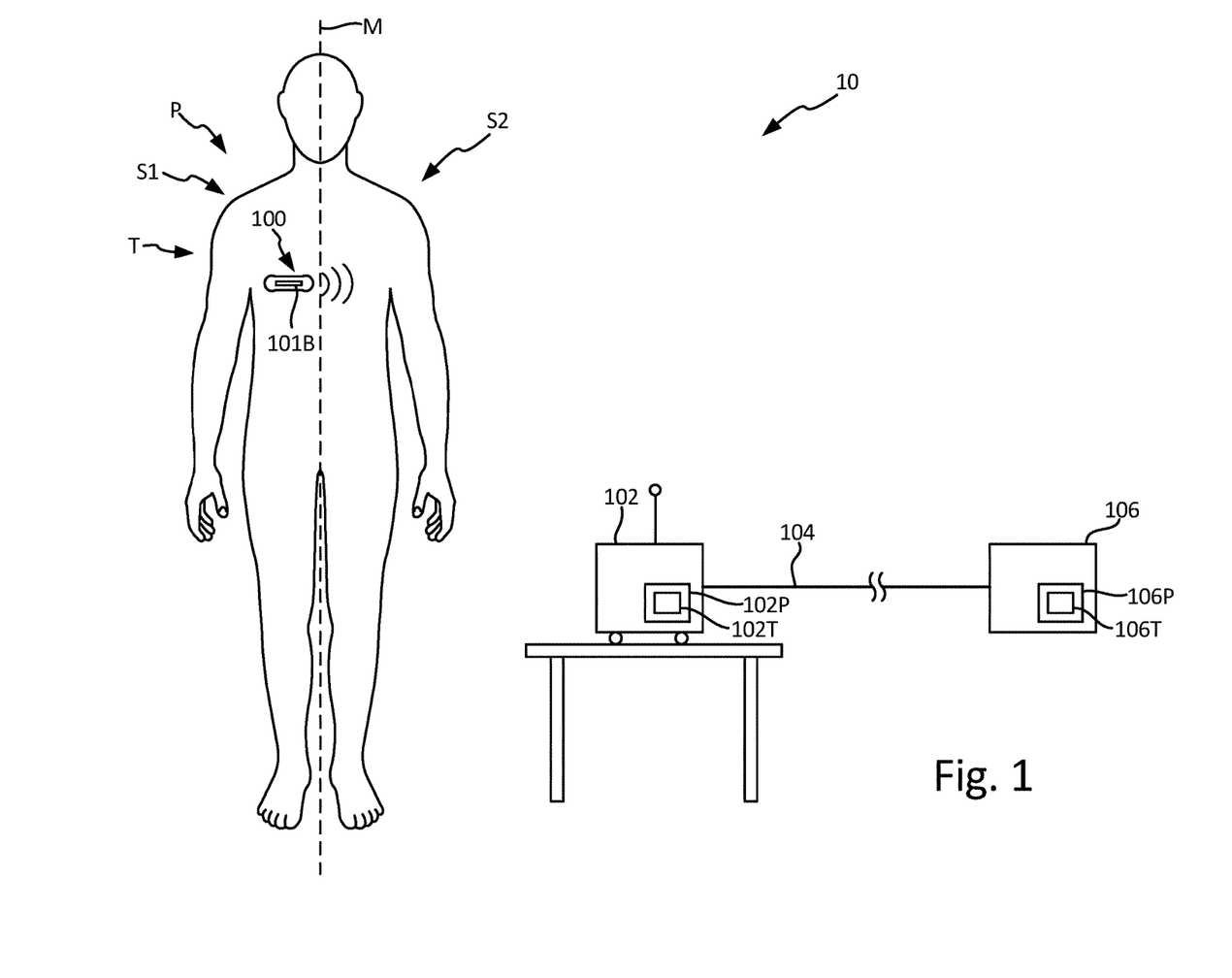
FIG. 1 illustrates a schematic view of a monitoring and/or treatment system that monitors electrocardiogram (ECG) signals and communicates ECG episodes representative of detected arrhythmias to a monitoring center according to an embodiment of the present invention.

FIG. 1 illustrates a patient P and a monitoring system 10, according to one or more embodiments of the present disclosure for monitoring cardiac activity. Patient P comprises a midline M, a first side S1, for example a right side, and a second side S2, for example a left side. Monitoring system 10 comprises a patient medical device 100, gateway 102, and remote monitoring center 106. In the embodiment shown in FIG. 1, patient medical device 100 is an adherent device that attaches to the skin of the patient, but in other embodiments may be an implantable device, an insertable device, an injectable device, or a wearable device such as a Holter monitor (collectively referred to as a medical device). Each of these devices has advantages and disadvantages, in terms of battery life, memory, communication capabilities, etc. For example, injectable devices have limited on-board memory that may be insufficient to store all detected arrhythmic ECG segments. As a result, older arrhythmic ECG segments may be overwritten by newer ECG segments. Utilizing rate-based sensitivity/specificity levels identifies more clinically relevant arrhythmic ECG segments to be captured, and therefore better utilizes the limited on-board memory associated with an injectable device. Likewise, some adherent devices utilize wireless/cellular communication to communicate arrhythmic ECG segments to a remote monitoring center. However, there is a cost of communicating detected arrhythmic ECG segments, which includes the time required for a HCP to review each communicated ECG segment. In this way, even if in one application memory is not as limited as in others, identifying clinically relevant ECG segments is still advantageous, albeit for different reasons. Exemplary embodiments of suitable medical devices are described in more detail with respect to FIGS. 6 and 7, below. In general, medical device 100 is described herein as providing a monitoring function, but in other embodiments may be configured to provide treatment as well.

Medical device 100 can be adhered/injected/inserted to a patient P at many locations, for example thorax T of patient P. In many embodiments, the device may adhere to one side of the patient, from which side data can be collected. A benefit of utilizing an adherent device, implantable, or injectable device is that it may be utilized to collect physiological data from the patient while the patient goes about normal day-to-day activities outside of a hospital setting. Medical device 100 may monitor a number of physiological parameters associated with patient P, including electrocardiogram (ECG) signals utilized to detect rhythm abnormalities such as tachycardia and/or bradycardia as well as activity level data, posture, bio-impedance, etc. Analysis of the ECG signals to detect rhythm abnormalities may be done locally by medical device 100 or remotely by gateway 102 and/or remote monitoring center 106 (or similar platform separate from medical device 100).

In embodiments in which the ECG signals are analyzed locally by medical device 100, heart-rate thresholds and rate-dependent sensitivity/specificity levels are utilized to detect rhythm abnormalities such as a tachycardia/bradycardia. In response to a detected rhythm abnormality, medical device 100 captures/stores an ECG segment corresponding with the detected abnormality. The captured ECG segment is subsequently transmitted to remote monitoring center 106 for review by a human HCP. Communication of the captured ECG segment may be immediate, or may be delayed for a period of time (i.e., until it is possible/cost effective to communicate the stored ECG segment). In response to the received ECG samples, the HCP may verify the detected rhythm abnormality and take appropriate steps (e.g., prescribe treatment).

In other embodiments in which ECG signals are not analyzed by medical device 100 locally, monitored ECG signals are communicated to an external processor such as gateway 102 or remote monitoring center 106 for analysis and detection of rhythm abnormalities. As discussed above, gateway 102 and/or remote monitoring center 106 utilizes heart-rate thresholds and rate-dependent sensitivity/specificity thresholds to detect rhythm abnormalities such as a tachycardia/bradycardia. In response to a detected rhythm abnormality, an ECG segment corresponding with the detected abnormality is captured and stored for subsequent review by a HCP.

In the embodiment shown in FIG. 1, medical device 100 communicates wirelessly with remote center 106. The communication may occur directly (via a cellular or Wi-Fi network), or indirectly through intermediate device or gateway 102. As described above, in one embodiment ECG signals monitored by medical device 100 are communicated in their entirety to remote center 106 for analysis. In other embodiments, medical device 100 processes the monitored ECG signals locally using heart-rate thresholds and rate-dependent sensitivity/specificity thresholds to detect rhythm abnormalities and stores/captures ECG segments corresponding with detected abnormalities.

In one embodiment, gateway 102 comprises components of the zLink™, a small portable device similar to a cell phone that wirelessly transmits information received from medical device 100 to remote monitoring center 106. The gateway 102 may consist of multiple devices, which can communicate wired or wirelessly with remote center 106 in many ways, for example with a connection 104 which may comprise an Internet connection and/or with a cellular connection. Remote center 106 may comprise a hosted application for data analysis and storage that also includes a website, which enables secure access to physiological trends and clinical event information for interpretation and diagnosis. Remote center 106 may further or alternatively comprise a back-end operation where physiological data from adherent device 100 are read by human experts to verify accuracy. Reports may then be generated at remote monitoring center 106 for communication to the patient's physician or care provider. In one embodiment, in addition to one-way communication from medical device 100 to gateway 102 and/or remote monitoring center 106, remote monitoring center 106 may communicate/push heart-rate thresholds and/or rate-dependent sensitivity/specificity thresholds to medical device 100, either to program/initialize medical device 100 or update the values stored by medical device 100.

In an exemplary embodiment, monitoring system 10 comprises a distributed processor system with at least one processing module (not shown) included as part of adherent device 100, at least one processor 102P of gateway 102, and at least one processor 106P at remote center 106, each of which processors can be in electronic communication with the other processors. At least one processor 102P comprises a tangible medium 102T, and at least one processor 106P comprises a tangible medium 106T. Remote processor 106P may comprise a backend server located at the remote center. Physiological parameters—including ECG samples—monitored by medical device 100 may be analyzed by one or more of the distributed processors included as part of medical device 100, gateway 102, and/or remote monitoring center 106.

Figure 2A:
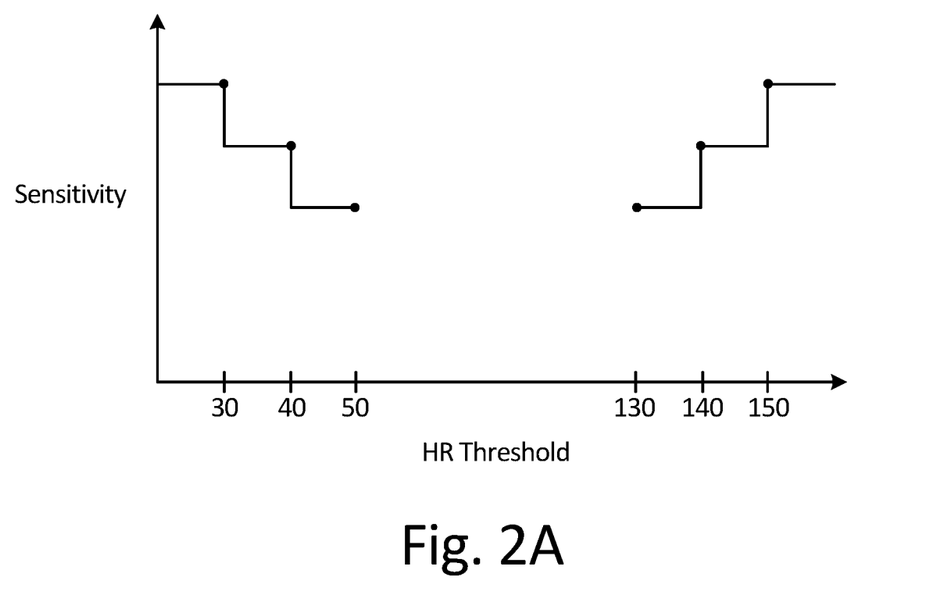
FIGS. 2a and 2b are charts illustrating rate-dependent sensitivity and specificity thresholds, respectively, utilized for arrhythmia detection according to an embodiment of the present invention.
Figure 2B:
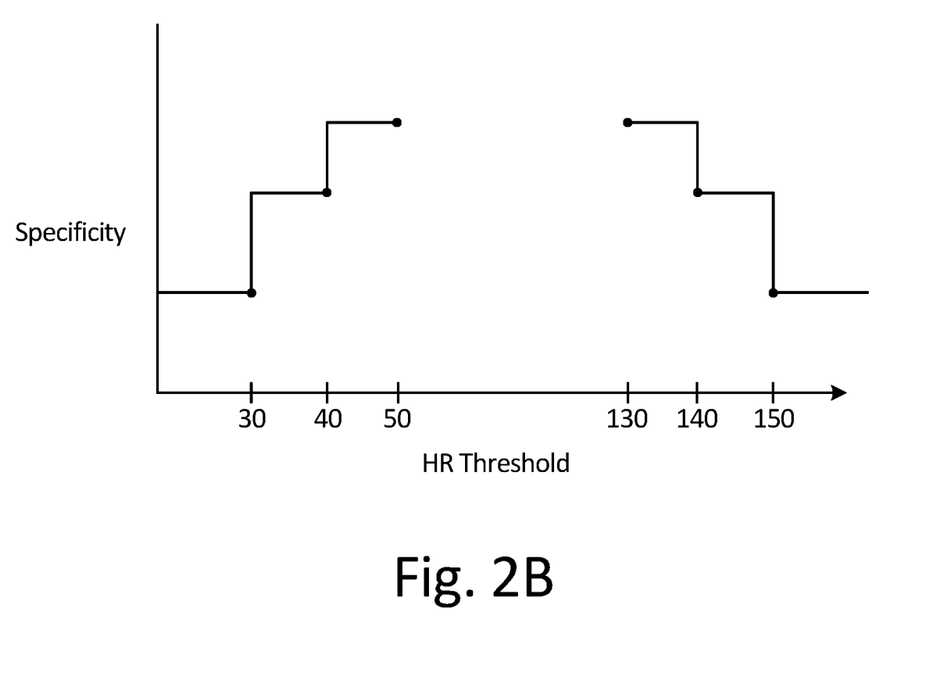

FIGS. 2a and 2b are charts illustrating rate-dependent sensitivity and specificity thresholds, respectively, utilized for arrhythmia detection according to an embodiment of the present invention. In particular, the charts illustrate the reciprocal relationship between sensitivity and specificity, and the assumption that higher rate tachycardia events are more clinically relevant than lower rate tachycardia events (and that lower rate bradycardia events are more clinically relevant than higher rate bradycardia events). In the embodiment shown in FIGS. 2a and 2b, a plurality of heart-rate thresholds are selected (e.g., bradycardia thresholds at 30 BPM, 40 BPM, and 50 BPM, and tachycardia thresholds at 130 BPM, 140 BPM, and 150 BPM), although in other embodiments additional or fewer threshold values may be utilized, and threshold values may be selected at any heart rate desired. As discussed in more detail below, in one embodiment heart-rate thresholds are selected based on one or more patient characteristics or one or more physiological parameters monitored with respect to the patient. Similarly, additional or fewer heart-rate thresholds may be utilized each having an assigned sensitivity/specificity level.

In the embodiment shown in FIG. 2a, rate-dependent sensitivity levels are defined for both bradycardia and tachycardia event detection. With respect to tachycardia events, a higher rate tachycardia may be more clinically significant than a lower rate tachycardia. Hence, in the embodiment shown in FIG. 2a, higher rate tachycardia thresholds are assigned higher sensitivity levels. For example, a tachycardia event exceeding 150 BPM (referred to as a tachy150) is assigned a higher sensitivity than a tachycardia exceeding 140 BPM (i.e., tachy240), which in turn is assigned a higher sensitivity level than a tachycardia exceeding 130 BPM (i.e. tachy130). As a result, the higher sensitivity associated with higher rate tachycardia threshold reduces the risk of missing a true positive event (e.g., tachy150 event), but at a cost of identifying more false positive tachy150 events. Conversely, the lower sensitivity level associated with lower rate tachycardia thresholds reduces false positives associated with—at least in this embodiment—clinically less relevant tachycardia events.

Likewise, with respect to bradycardia events, a lower rate bradycardia may be more clinically significant than a higher rate bradycardia. Hence, in the embodiment shown in FIG. 2a, lower rate bradycardia thresholds are assigned higher sensitivities. For example, bradycardia event less than 30 BPM (referred to as a brady30 event) is assigned a higher sensitivity than a bradycardia event less than 40 BPM (i.e., brady40), which in turn is assigned a higher sensitivity than a bradycardia less than 50 BPM (i.e. brady50). As a result, the higher specificity associated with lower rate bradycardia events reduces the risk of missing a true positive event (e.g., brady30 event), but at a cost of identifying more false positive brady30 events. This higher sensitivity ensures potentially more clinically relevant brady30 events are not missed.

FIG. 2b illustrates the reciprocal relationship between sensitivity and specificity. For example, the highest rate tachycardia (tachy150) is assigned a specificity that is lower than the specificity assigned to tachycardia exceeding 140 BPM (tachy140), which in turn is assigned a lower specificity than a tachycardia exceeding 130 BPM (i.e. tachy130). Likewise, with respect to bradycardia events, a bradycardia event less than 30 BPM (referred to as a brady30 event) is assigned a lower specificity than a bradycardia less than 40 BPM (i.e., brady40), which in turn is assigned a lower specificity than a bradycardia less than 50 BPM (i.e. brady50). As a result, the lower specificity associated with lower rate bradycardia events increases the risk of a false positive event (e.g., normal sinus rhythm classified incorrectly as a brady30 event), but minimizes the risk of failing to identify a brady30 event.

Figure 3:
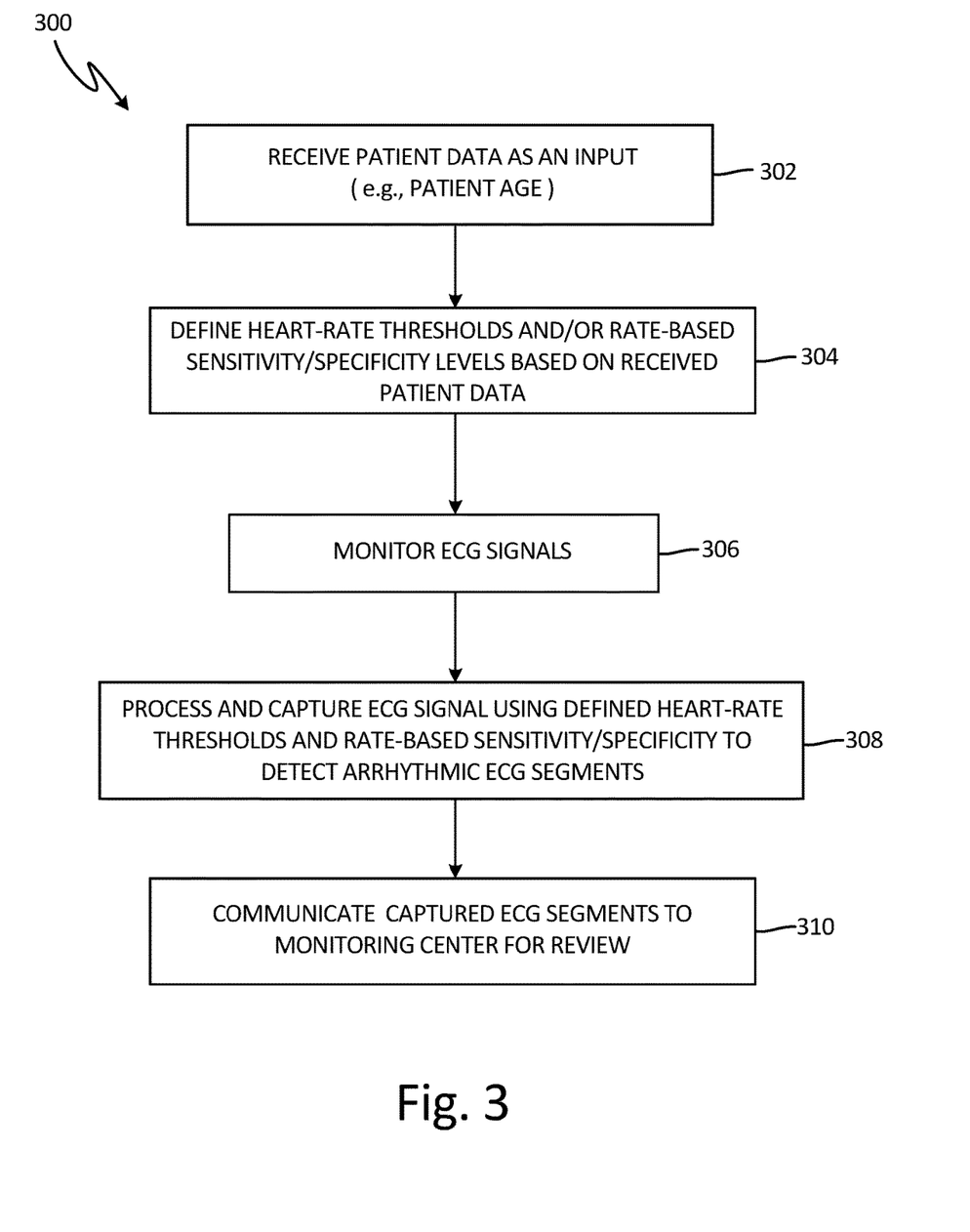
FIG. 3 is a flowchart that illustrates a method of personalizing heart-rate thresholds and rate-based sensitivity/specificity based on received patient data according to an embodiment of the present invention.

FIG. 3 is a flowchart that illustrates a method of personalizing arrhythmic thresholds and rate-based sensitivity/specificity based on received patient data according to an embodiment of the present invention. Patient data may include a variety of characteristics related to the patient, including patient age, weight, sex, resting heart rate, etc. The embodiment shown in FIG. 3 utilizes patient data (e.g., patient age in this example) as an input for personalizing arrhythmic thresholds, however, it should be understood that in other embodiments various other patient characteristics may be utilized either alone or in combination with patient age to personalize arrhythmic thresholds.

At step 302, patient data is received as an input. In the embodiment shown in FIG. 3, the input is related to the age of the patient, but as discussed above may include other patient data. The input may be received by the monitoring device directly, or may be received external to the monitoring device (e.g., remote monitoring center) capable of updating the heart-rate thresholds and/or rate-based sensitivity/specificity of the monitoring device. At step 304, heart-rate thresholds are defined based on the received patient data. In the embodiment shown in FIG. 3, patient age is utilized to personalize the heart-rate thresholds utilized to analyze ECG signals. Table 1 illustrates the personalization of the heart-rate thresholds according to an embodiment of the present invention.

TABLE 1

| Personalized Heart-Rate Thresholds | Rate-Based Sensitivity/Specificity Levels |
|---|---|
| High Rate Tachycardia (e.g., Age Predicted Maximal Heart Rate + 5 BPM) | Higher Sensitivity Level (e.g., X/Y small) |
| Medium Rate Tachycardia (e.g., Age Predicted Maximal Heart Rate - 10) BPM) | Medium Sensitivity Level (e.g., X/Y medium) |
| Low Rate Tachycardia (e.g., Age Predicted Maximal Heart Rate - 30 BPM) | Lower Sensitivity Level (e.g., X/Y high) |
| Low Rate Bradycardia (e.g., Min(Max (Age-25, 15), 60) BPM) | Higher Sensitivity Level (e.g., X/Y small) |
| Medium Rate Bradycardia (e.g., Min(Max(Age-15, 15), 60) BPM) | Medium Sensitivity Level (e.g., X/Y medium) |
| High Rate Bradycardia (e.g., Min(Max (Age-5, 15), 60) BPM | Lower Sensitivity Level (e.g., X/Y high) |

In the embodiment shown in Table 1, the heart-rate thresholds defined with respect to tachycardia detection is based on the age-predicted maximal heart rates. The highest rate tachycardia threshold is assigned the highest sensitivity level. As the tachycardia rate decreases (in this case, for the medium rate tachycardia and low rate tachycardia) the sensitivity level is lowered. With respect to the heart-rate thresholds defined with respect to tachycardia detection, the patient's age is utilized to select an age-predicted maximal heart rate, which in turn is utilized to select the various tachycardia heart-rate thresholds. With respect to the heart-rate thresholds defined with respect to bradycardia detection, the patient's age is used to directly to determine the various bradycardia heart-rate thresholds. For example, the low rate bradycardia threshold is defined as (Min(Max(Age-25,15), 60) BPM). For a patient that is seventy years old, the equation is defined as (Min(Max(70-25,15),60) BPM), which corresponds to a low-rate bradycardia threshold of forty-five (45) BPM. For a patient that is thirty years old, the equation would correspond to a low-rate bradycardia threshold of fifteen (15) BPM. In other embodiments, other patient characteristics may be utilized to define the various heart-rate thresholds.

In embodiments in which patient data is received external to the monitoring device, then at step 304 the personalized arrhythmic thresholds are communicated to the monitoring device. In embodiments in which patient data is provided directly to medical device 100, then medical device 100 calculates the personalized arrhythmic thresholds according to calculations such as those shown in Table 1. In other embodiments, in which processing of ECG signals is performed remotely from medical device 100, then personalized arrhythmic thresholds are provided to the computer/device responsible for processing ECG signals from the corresponding patient.

At step 306, ECG data is monitored by medical device 100. At step 308, the monitored ECG signals are processed/analyzed using the personalized heart-rate thresholds and rate-based sensitivity levels defined based on the patient data to detect arrhythmic ECG segments. As discussed above, processing/analysis of ECG data may be done locally by medical device 100 or remotely—for example at gateway 102 or remote monitoring center 106.

At step 310, arrhythmic ECG segments—if processed locally by medical device 100—are communicated to remote monitoring center 106 for review by a HCP. Utilization of patient data to personalize heart-rate thresholds and rate-based sensitivity/specificity thresholds results in a higher percentage of clinically relevant ECG segments being provided to remote monitoring center for review. A benefit of this approach is that fewer ECG segments are provided to the remote monitoring center for review, but while retaining sensitivity/specificity balance that ensures clinically relevant ECG segments are reviewed by a HCP.

Figure 4:
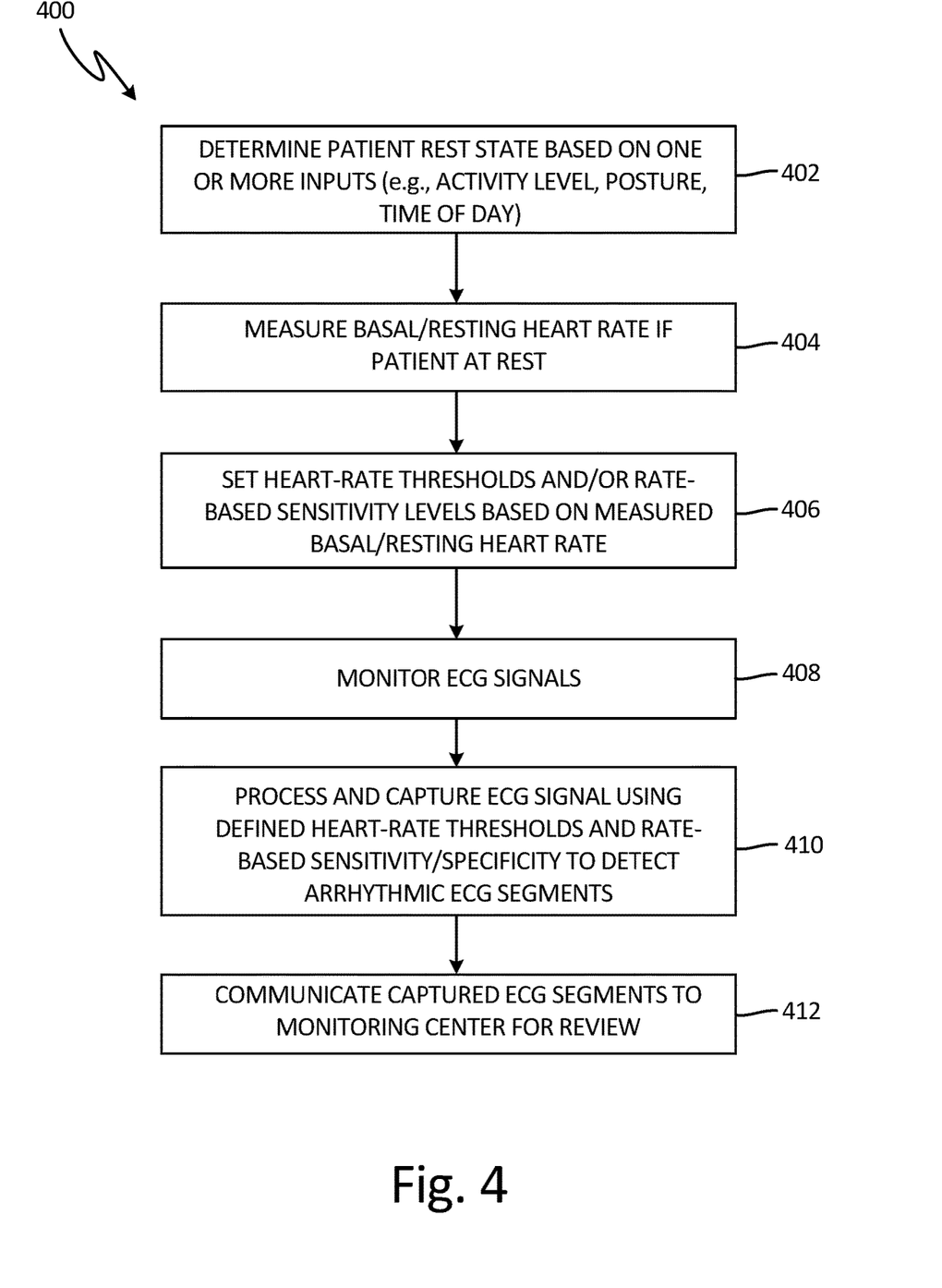
FIG. 4 is a flowchart that illustrates a method of personalizing heart-rate thresholds and rate-based sensitivity/specificity based on received patient data according to another embodiment of the present invention.

FIG. 4 is a flowchart that illustrates another method of personalizing heart-rate thresholds and rate-based sensitivity/specificity based on received patient data according to an embodiment of the present invention. In the embodiment shown in FIG. 4, patient data is based on a physiological parameter monitored by medical device 100. For example, the embodiment shown in FIG. 4 monitors basal/resting heart of the patient, and determines the personalized arrhythmic thresholds and rate-based sensitivity levels based on the monitored basal/resting heart rate.

At step 402, monitoring device determines whether the patient is at rest. This determination may be based on one or more monitored physiological parameters (e.g., activity level, posture, sleep status, etc.), or may be based on external factors such as time of day, patient location, or patient input). These inputs may be utilized alone or in combination with one another. For example, in one embodiment patient activity level and/or posture is determined based on accelerometer measurements taken by medical device 100. If the accelerometer measurements indicate the patient is not moving, or is in a prone position, then a determination is made that the patient is at rest. Similarly, a determination that the patient is at rest may take into account the local time, and utilize a time (e.g., between 12:00 and 4:00 in the morning) in which it is suspected that the patient is sleeping to measure the basal/resting heart rate of the patient. In yet other embodiments, input is received from the patient or physician indicating the patient is in a rest state. For example, a patient being outfitted with a medical device 100 at the physician's office may indicate a resting state during which a basal/resting heart rate may be measured. In some embodiments, additional calibration steps may be utilized. For example, the patient may be instructed to remain sitting for a period of time (e.g., 5 minutes), then instructed to walk for a period of time (e.g., 5 minutes), following by another period of sitting. Average heart rate data is collected during these periods of time in order to determine the basal/resting heart to be utilized on a patient-by-patient basis.

At step 404, having determined that the user is in a rest state, the basal/resting heart rate of the patient is measured. In one embodiment, the heart rate of the patient is monitored for a period of time and averaged to determine the basal/resting heart rate of the patient.

At step 406 heart-rate thresholds and/or rate-based sensitivity levels are defined based on the monitored basal/resting heart rate of the patient. Table 2 illustrates the personalization of the heart rate thresholds (i.e., arrhythmic thresholds) and corresponding rate-based sensitivity/specificity levels according to an embodiment of the present invention.

TABLE 2

| Personalized Heart-Rate Thresholds | Rate-Based Sensitivity/Specificity Levels |
|---|---|
| High Rate Tachycardia (e.g., Basal/Resting Heart Rate + 110 BPM) | Higher Sensitivity Level (e.g., X/Y small) |
| Medium Rate Tachycardia (e.g., Basal/Resting Heart Rate + 100 BPM) | Medium Sensitivity Level (e.g., X/Y medium) |

TABLE 2-continued

| Personalized Heart-Rate Thresholds | Rate-Based Sensitivity/Specificity Levels |
| --- | --- |
| Low Rate Tachycardia (e.g., Basal/Resting Heart Rate + 90 BPM) | Lower Sensitivity Level (e.g., X/Y high) |
| Low Rate Bradycardia (e.g., Basal/Resting Heart Rate - 40 BPM) | Higher Sensitivity Level (e.g., X/Y small) |
| Medium Rate Bradycardia (e.g., Basal/Resting Heart Rate - 30 BPM) | Medium Sensitivity Level (e.g., X/Y medium) |
| High Rate Bradycardia (e.g., Basal/Resting Heart Rate - 20 BPM | Lower Sensitivity Level (e.g., X/Y high) |

In the embodiment shown in Table 2, the heart-rate thresholds defined with respect to tachycardia detection are based on the monitored basal/resting heart rate monitored with respect to the patient. The highest rate tachycardia is assigned the highest sensitivity level. As the tachycardia rate decreases (in this case, for the medium rate tachycardia and low rate tachycardia) the sensitivity level is lowered. With respect to the heart-rate thresholds defined with respect to bradycardia detection, the monitored basal/resting heart rate is similarly employed in the calculation of the various bradycardia thresholds. For example, the low rate bradycardia threshold is defined as Basal/Resting Heart Rate—40 BPM. For a patient that having a resting heart rate of 65 BPM, the low rate bradycardia threshold is set equal to 25 BPM.

In the embodiment shown in FIG. 4, medical device 100 measures the basal/resting heart rate of the patient, and therefore may determine the thresholds utilized locally based on the monitored basal/resting heart rate. In embodiments in which processing of the ECG signals is done remotely, then monitoring device may similarly communicate the measured basal/resting heart rate to the remote monitoring center to define the arrhythmic thresholds and rate-based sensitivity levels.

At step 408, ECG data is monitored by medical device 100. At step 410, the monitored ECG signals are processed/analyzed using the personalized arrhythmic thresholds and rate-based sensitivity levels defined based on the measured basal/resting heart rate. As discussed above, processing/analysis of ECG data may be done locally by medical device 100 or remotely—for example at gateway 102 or remote monitoring center 106.

At step 412, arrhythmic ECG segments—if processed locally by medical device 100—are communicated to remote monitoring center 106 for review by a HCP. Utilization of measured basal/resting heart rate of the patient to personalize heart-rate thresholds and rate-based sensitivity/specificity thresholds results in a higher percentage of clinically relevant ECG segments being provided to remote monitoring center for review. Once again, a benefit of this approach is that clinically relevant ECG segments are reviewed by a HCP, or reviewed with higher-priority by the HCP. In other embodiments, arrhythmic ECG segments are not communicated to a remote monitoring center but are instead stored locally. For example, in one embodiment implantable devices may not utilize communicate arrhythmic ECG segments, but rather may store captured segments until such time the segments can be downloaded for review. In some of these embodiments, memory is limited, and may result in older stored ECG segments being overwritten by newer segments. In one embodiment, identification of ECG segments as more clinically relevant than others allows for those more clinically relevant ECG segments to avoid being overwritten. For example, triggering of an ECG segment with a lower sensitivity level results in a more clinically relevant ECG segment than one triggered (assuming the same heart-rate threshold) using a higher sensitivity level. As a result, the ECG segment captured using the lower sensitivity level may be retained in memory over other, less clinically relevant ECG segments.

Figure 5:
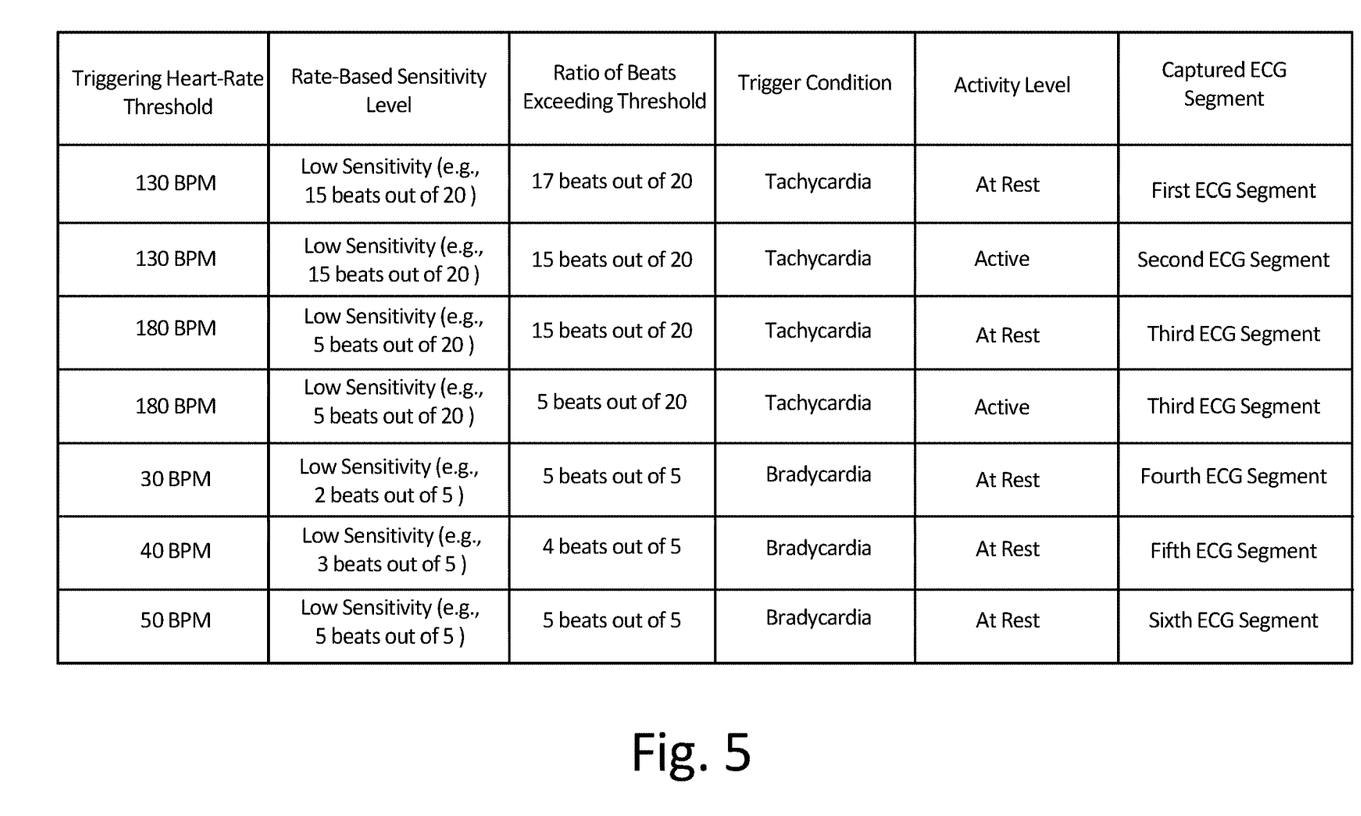
FIG. 5 is a data structure utilized at remote monitoring center according to an embodiment of the present invention to allow a health care professional (HCP) to filter/search through captured ECG segments.

FIG. 5 is a data structure utilized at remote monitoring center according to an embodiment of the present invention to allow a HCP to filter/search through captured ECG segments. Each data record is comprised of a captured ECG segment, along with additional information or data tags that provide additional information to the HCP regarding the captured ECG segment. In the embodiment shown in FIG. 5, tags include corresponding heart-rate threshold utilized to trigger capture of the ECG segment (e.g., brady30, tachy150, etc.), rate-based sensitivity level (e.g., high sensitivity, low sensitivity, etc.), ratio of beats exceeding the heart-rate threshold (e.g., 15 out of 20 beats), trigger condition (e.g., tachycardia, bradycardia, etc.), patient activity level (e.g., active, at rest), and ECG segment to be reviewed. Additional data/information provided in the tags associated with each captured ECG segment allows a HCP to filter/search ECG segments based on these tags. For example, a HCP such as a physician may be most interested in tachycardia conditions detected while a patient is at rest, and could therefore use the activity level tag in combination with the trigger condition field to identify ECG segments relevant to the reviewing HCP.

In the embodiment shown in FIG. 5, the tags associated with the first ECG segment describe the heart-rate threshold utilized to trigger capture of the ECG segment as 130 BPM. The rate-based sensitivity level is identified as being low-sensitivity (e.g., 15 beats out of 20 required to exceed the heart-rate threshold). In one embodiment, this may include a numerical representation of the sensitivity (e.g., X/Y) or simply a description of the rate-based sensitivity level (e.g., high, medium, low). In addition, the first record lists the ratio of beats measured as exceeding the arrhythmic threshold (e.g., 17 beats out of 20), even though the sensitivity level only required 15 beats out of 20. This may be particularly with respect to triggering thresholds using relatively high sensitivity thresholds such as that shown with respect to the third ECG segment, in which only 5 beats out of 20 are required to trigger capture of the ECG segment, but in fact 15 beats out of 20 were measured as exceeding the threshold. This may indicate a particularly relevant ECG segment that merits immediate review and consideration by a HCP. In addition, the trigger condition (e.g., tachycardia, bradycardia, etc.) may be provided, as well as other information such as other monitored physiological parameters (e.g., activity level of the patient at the time the ECG segment was captured). For example, activity level of the patient (e.g., at rest, or active) may be important to a HCP reviewing tachycardia events, wherein lower rate tachycardia events detected while a patient is active may be less clinically relevant than lower rate tachycardia events detected while a patient is at rest. A benefit of including one of more of these tags with the captured ECG segment is that it allows the HCP reviewing the captured ECG segments to focus on those of potential highest importance, as opposed to reviewing the ECG segments in the order they occur.

In one embodiment, the records may be coded according to relevance to aid a HCP in reviewing the captured ECG segments. This may include automatic ordering of the ECG segments according to a predetermined criteria (e.g., high sensitivity ECG segments first, ordered by the rest state of the patient and the ratio of beats exceeding the threshold), or may include color-coding of the ECG segments according to clinical relevance.

In one embodiment, utilizing a data structure such as that shown in FIG. 5 improves the ability of a HCP to sort and filter ECG segments to review those holding the most clinical relevance. As a result, depending on the cost of capturing/communicating ECG segments from a monitoring device to a remote monitoring center, it may be advantageous to capture all potentially relevant ECG segments (i.e., increase rate-based sensitivities) and rely more heavily on the ability to sort/filter using the tags. That is, it may be advantageous to capture all potentially relevant ECG segments, and utilize the information associated with each captured ECG segment to aid the HCP in locating those that are most clinically relevant.

Figure 6:
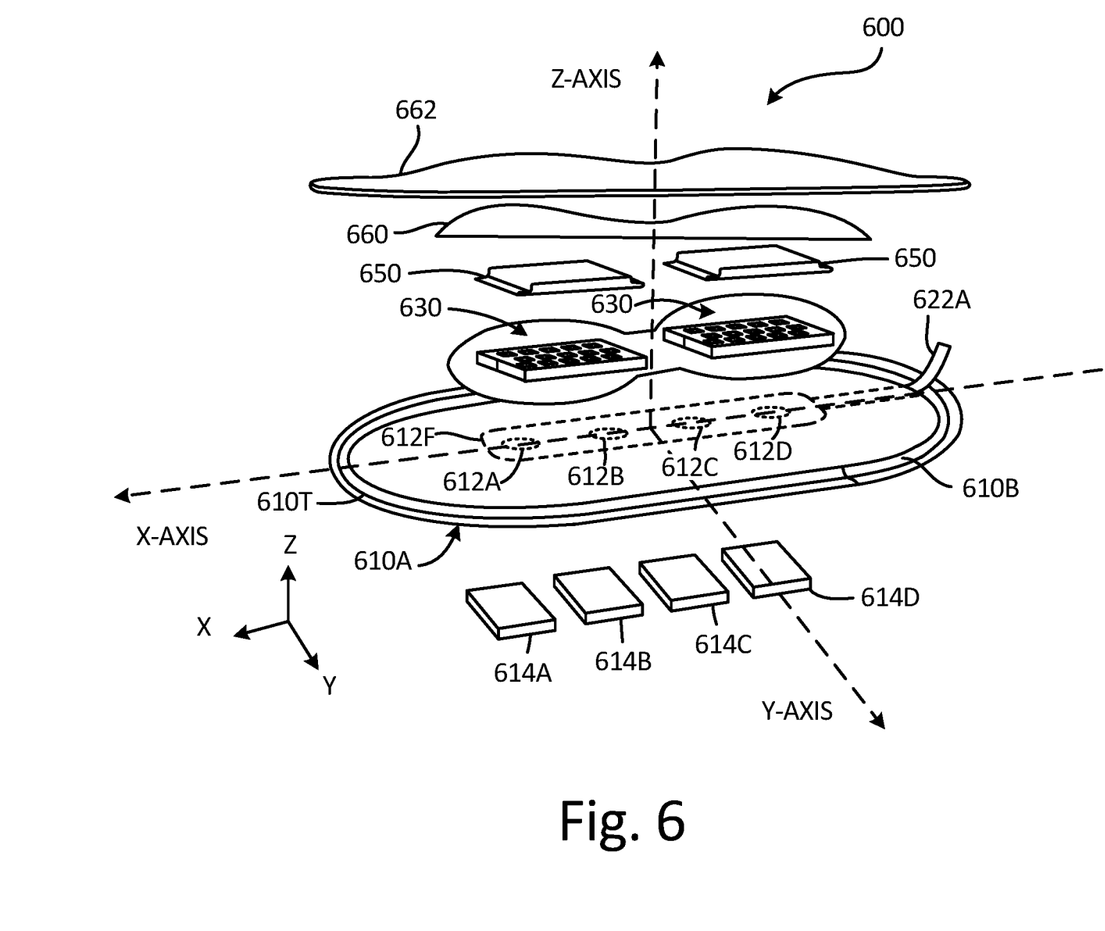
FIG. 6 is an exploded view of an adherent monitoring device utilized to monitor and detect ECG episodes according to an embodiment of the present invention.

FIG. 6 is an exploded view, respectively, of monitoring device 600 with rate-based sensitivity detection, according to one or more embodiments of the present disclosure. In the embodiment shown in FIG. 6, monitoring device 600 is an adherent device, but as described above may also be implemented as an implantable device, an injectable device, or similar wearable device. In the embodiment shown in FIG. 6, adherent device 600 includes adherent tape 610T, electrodes 612A, 612B, 612C, 612D with gels 614A, 614B, 614C, 614D, printed circuit board (PCB) 620, flexible connected 622A, electrical components/sensors 630 mounted on PCB 620, batteries 650, electronics housing cover 660, and flexible cover 662.

Adherent device 600 comprises at least two electrodes—although the embodiment shown in FIG. 6 includes electrodes 612A, 612B, 612C and 612D. Adherent device 600 may comprise a maximum dimension, for example a maximum length from about 4 to 10 inches, a maximum thickness along a profile of the device from about 0.2 inches to about 0.6 inches, and a maximum width from about 2 to about 4 inches. The adherent patch 600 comprises a first side, or a lower side 610A, that is oriented toward the skin of the patient when placed on the patient. The adherent patch 600 may also comprise a tape 610T which is a material, preferably breathable, with an adhesive (not shown) to adhere to patient P. Electrodes 612A, 612B, 612C and 612D are affixed to adherent patch 600. In many embodiments, at least four electrodes are attached to the patch. Gels 614A, 614B, 614C and 614D can each be positioned over electrodes 612A, 612B, 612C and 612D, respectively, to provide electrical conductivity between the electrodes and the skin of the patient. Adherent patch 600 also comprises a second side, or upper side 610B. In many embodiments, electrodes 612A, 612B, 612C and 612D extend from lower side 610A through adherent patch 100 to upper side 610B. An adhesive can be applied to upper side 610B to adhere structures, for example a breathable cover, to the patch such that the patch can support the electronics and other structures when the patch is adhered to the patient. In many embodiments, adherent patch 100 may comprise a layer of breathable tape 610T, for example a tricot-knit polyester fabric, to allow moisture vapor and air to circulate to and from the skin of the patient through the tape. Electrical signals received at electrodes 612A-612D may be communicated to electronic components 630 via flexible connection 622A, which is connected to a PCB (not shown). Cover 660 is positioned over batteries 650 and electronic components 630 to provide protection for both. In addition, flexible cover 662 is positioned to encase the flexible PCB 620, electronics components 630, and/or adherent patch 610 so as to protect at least the electronics components and the PCB In addition, electronic components 630 may include ECG circuitry utilized to generate electrocardiogram signals and data from two or more of electrodes 612A, 612B, 612C and 612D in many ways. In some embodiments, ECG circuitry (not shown) is connected to inner electrodes 612B and 612C, which may comprise sense electrodes of the impedance circuitry as described above. In many embodiments, the ECG circuitry may measure the ECG signal from electrodes 612A and 612D when current is not passed through electrodes 612A and 612D. In addition, electronic components 630 may include bioimpedance circuitry connected to two or more of electrodes 612A, 612B, 612C and 612D to allow electronic components 630 to measure a bioimpedance associated with the patient. In addition, electronic components 630 may include an accelerometer configured to measured motion of the patient.

In addition, electronic circuitry 630 may comprise a processor module that can be configured to analyze physiological parameters monitored by adherent device 600 and to control collection and transmission of data from the electrocardiogram circuitry. In one embodiment, the processor module included as part of electronic circuitry 630 comprises a tangible medium, for example read only memory (ROM), electrically erasable programmable read only memory (EEPROM) and/or random access memory (RAM). Tangible medium may, for example, store heart-rate thresholds to be utilized, as well as rate-based sensitivity levels to be utilized in combination with each heart-rate threshold. Processing of monitored physiological parameters such as ECG signals may be distributed between the local processor module included as part of electronic circuitry 630 and remote monitoring system 106 (shown in FIG. 1).

In one embodiment, a processor and/or a processing module include electronic circuitry configured to process monitored ECG signals of a patient, detect rhythm abnormalities (e.g., bradycardia, tachycardia, etc.) for a plurality of threshold heart rates, capture clinically relevant ECG episode based on the rate-based sensitivity levels associated with each of the plurality of threshold heart rates. The processor and/or processing module may also communicate and/or transmit ECG signals and/or captured ECG segments to a remote monitoring center for review by an analysis.

In many embodiments, electronics components 630 comprise wireless communications circuitry (not shown) to communicate with remote center 106. The PCB (not shown) may comprise an antenna to facilitate wireless communication. The antenna may be integral with the PCB or may be separately coupled thereto. The wireless communication circuitry can be coupled to the electrocardiogram circuitry to transmit to a remote center with a communication protocol at least one of the electrocardiogram signal or other features collected by the adherent device 600. In specific embodiments, the wireless communication circuitry is configured to transmit collected physiological parameters to remote center 106 (shown in FIG. 1) either directly or through gateway 102. The communication protocol comprises at least one of Bluetooth, ZigBee, WiFi, WiMAX, IR, amplitude modulation or frequency modulation. In many embodiments, the communications protocol comprises a two-way protocol such that the remote center is capable of issuing commands to control data collection. For example, in one embodiment a health care professional (HCP) (such as a HCP) may push updated heart-rate thresholds and/or rate-based sensitivity levels to adherent device 600. For example, a HCP may increase the rate-based sensitivity levels associated with one or more heart-rate thresholds in response to few ECG segments being captured. Conversely, in response to a high number of ECG segments being captured, a HCP may decrease the rate-based sensitivity levels associated with one or more heart-rate thresholds.

Figure 7:
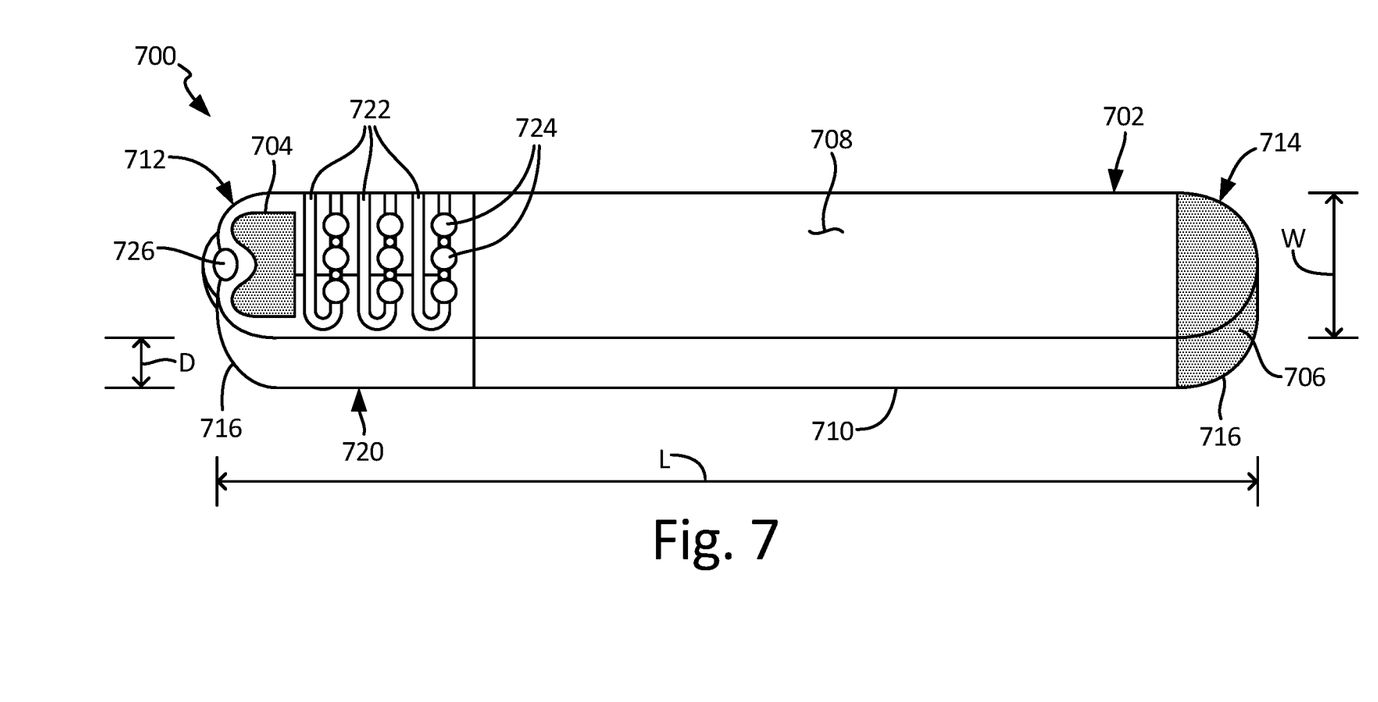
FIG. 7 is a perspective view of an insertable monitoring device utilized to monitor and detect ECG episodes according to an embodiment of the present invention.

FIG. 7 is a perspective view of an insertable monitoring device 700 according to an embodiment of the present invention. In the embodiment shown in FIG. 7, insertable cardiac monitor 700 is defined by a length L, a width W and thickness or depth D and is in the form of an elongated rectangular prism wherein the length L is much larger than the width W, which in turn is larger than the depth D. In one embodiment, the geometry of the insertable cardiac monitor 700—in particular a width W greater than the depth D—is selected to allow the cardiac monitor 700 to be inserted under the skin of the patient using a minimally invasive procedure and to remain in the desired orientation during insert. For example, the device shown in FIG. 7 includes radial asymmetries (notably, the rectangular shape) along the longitudinal axis that maintains the device in the proper orientation following insertion. For example, in one embodiment the spacing between proximal electrode 704 and distal electrode 706 may range from 30 millimeters (mm) to 55 mm, 35 mm to 55 mm, and from 40 mm to 55 mm and may be any range or individual spacing from 25 mm to 60 mm. In addition, insertable cardiac monitor 700 may have a length L that ranges from 30 mm to about 70 mm. In other embodiments, the length L may range from 40 mm to 60 mm, 45 mm to 60 mm and may be any length or range of lengths between about 30 mm and about 70 mm. In addition, the width W of major surface 708 may range from 3 mm to 10 mm and may be any single or range of widths between 3 mm and 10 mm. The thickness of depth D of cardiac monitor device 700 may range from 2 mm to 9 mm. In other embodiments, the depth D of insertable cardiac monitor 700 may range from 2 mm to 5 mm and may be any single or range of depths from 2 mm to 9 mm. In addition, insertable cardiac monitor 700 according to an embodiment of the present invention is has a geometry and size designed for ease of implant and patient comfort. Embodiments of insertable cardiac monitor 700 described in this disclosure may have a volume of three cubic centimeters (cm) or less, 1.5 cubic cm or less or any volume between three and 1.5 cubic centimeters.

In the embodiment shown in FIG. 7, once inserted within the patient, the first major surface 708 faces outward, toward the skin of the patient while the second major surface 710 is located opposite the first major surface 708. In addition, in the embodiment shown in FIG. 7, proximal end 712 and distal end 714 are rounded to reduce discomfort and irritation to surrounding tissue once inserted under the skin of the patient.

As described with other embodiments, proximal electrode 704 and distal electrode 706 are used to sense cardiac signals for determining abnormal cardiac events (e.g., bradycardia, tachycardia, etc.). ECG signals may be stored in a memory of the insertable cardiac monitor 700, and ECG data may be transmitted via integrated antenna 722 to another medical device, which may be another implantable device or an external device, or to a remote monitoring center. In alternative applications, electrodes 704 and 706 may be used for sensing any bio-potential signal of interest, which may be, for example, an EGM, EEG, EMG, or a nerve signal, from any implanted location.

In the embodiment shown in FIG. 7, proximal electrode 704 is in close proximity to the proximal end 712 and distal electrode 706 is in close proximity to distal end 714. In this embodiment, distal electrode 706 is not limited to a flattened, outward facing surface, but may extend from first major surface 708 around rounded edges 716 and onto the second major surface 710 so that the electrode 706 has a three-dimensional curved configuration. In the embodiment shown in FIG. 7, proximal electrode 704 is located on first major surface 708 and is substantially flat, outward facing. However, in other embodiments proximal electrode 704 may utilize the three dimensional curved configuration of distal electrode 706, providing a three dimensional proximal electrode (not shown in this embodiment). Similarly, in other embodiments distal electrode 706 may utilize a substantially flat, outward facing electrode located on first major surface 708 similar to that shown with respect to proximal electrode 704. The various electrode configurations allow for configurations in which proximal electrode 704 and distal electrode 706 are located on both first major surface 708 and second major surface 710. In other configurations, such as that shown in FIG. 7, only one of proximal electrode 704 and distal electrode 706 is located on both major surfaces 708 and 710, and in still other configurations both proximal electrode 704 and distal electrode 706 are located on one of the first major surface 708 or the second major surface 710 (i.e., proximal electrode 704 located on first major surface 708 while distal electrode 706 is located on second major surface 710). In another embodiment, insertable monitoring device 700 may include electrodes on both major surface 708 and 710 at or near the proximal and distal ends of the device, such that a total of four electrodes are included on insertable monitoring device 700. Electrodes 704 and 706 may be formed of a plurality of different types of biocompatible conductive material, e.g. stainless steel, titanium, platinum, iridium, or alloys thereof, and may utilize one or more coatings such as titanium nitride or fractal titanium nitride.

In the embodiment shown in FIG. 7, proximal end 712 includes a header assembly 720 that includes one or more of proximal electrode 704, integrated antenna 722, anti-migration projections 724, and/or suture hole 726. Integrated antenna 722 is located on the same major surface (i.e., first major surface 708) as proximal electrode 704 and is also included as part of header assembly 720. Integrated antenna 722 allows insertable monitoring device 700 to transmit and/or receive data. In other embodiments, integrated antenna 722 may be formed on the opposite major surface as proximal electrode 704, or may be incorporated within the housing 722 of insertable monitoring device 700. In one embodiment, electronic circuitry (not shown) may be housed within housing 722. As described above with respect to FIG. 6, electronic circuitry may include a tangible medium for storing the plurality of heart-rate thresholds and rate-based sensitivity levels. In addition, electronic circuitry may include sensing circuitry for sensing one or more physiological parameters, such as ECG signals, accelerometer signals, and/or bio-impedance signals, and may include a processor module for processing monitored ECG signals to detect arrhythmic ECG segments based on the heart-rate thresholds and rate-based sensitivity levels.

In the embodiment shown in FIG. 7, anti-migration projections 724 are located adjacent to integrated antenna 722 and protrude away from first major surface 708 to prevent longitudinal movement of the device. In the embodiment shown in FIG. 7, anti-migration projections 724 includes a plurality (e.g., nine) small bumps or protrusions extending away from first major surface 708. As discussed above, in other embodiments anti-migration projections 724 may be located on the opposite major surface as proximal electrode 704 and/or integrated antenna 722. In addition, in the embodiment shown in FIG. 7 header assembly 720 includes suture hole 726, which provides another means of securing insertable monitoring device 700 to the patient to prevent movement following insert. In the embodiment shown, suture hole 726 is located adjacent to proximal electrode 704. In one embodiment, header assembly 720 is a molded header assembly made from a polymeric or plastic material, which may be integrated or separable from the main portion of insertable monitoring device 700.

In this way, the disclosure provides a system and method for monitoring and processing electrocardiogram (ECG) signals to automatically capture clinically relevant ECG segments for subsequent review.

Discussion of Possible Embodiments

The following are non-exclusive descriptions of possible embodiments of the present invention.

A method of detecting arrhythmic electrocardiogram (ECG) signals comprises defining a plurality of threshold heart rates and rate-dependent sensitivity levels for detecting arrhythmic ECG episodes, wherein more clinically relevant heart rates are assigned rate-dependent sensitivity levels with higher sensitivities. The method may further include monitoring ECG signals associated with a patient using a monitoring device and processing the monitored ECG signals using the plurality of threshold heart rates and rate-dependent sensitivity levels to detect and capture arrhythmic ECG segments.

The method of the preceding paragraph can optionally include, additionally and/or alternatively any, one or more of the following features, configurations and/or additional components.

The method may further include wherein the monitoring device processes the monitored ECG signals locally, and wherein captured arrhythmic ECG segments are communicated to a remote monitoring center for review.

The method may further include wherein monitored ECG signals are communicated to a remote monitoring center for processing of the monitored ECG signals using the plurality of threshold heart rates and rate-dependent sensitivity levels.

The method may further include wherein the plurality of threshold heart rates include a plurality of heart rate thresholds associated with tachycardia thresholds and a plurality of heart rate thresholds associated with bradycardia thresholds. The method may further include wherein higher rate tachycardia thresholds are assigned a higher sensitivity level than lower rate tachycardia thresholds, and lower rate bradycardia thresholds are assigned a higher sensitivity level than higher rate bradycardia thresholds.

The method may further include wherein the plurality of heart rate thresholds are selected based on one or more patient characteristics.

The method may further include wherein the one or more patient characteristics include one or more of patient age, weight, sex, and/or basal/resting heart rate.

The method may further include determining whether the patient is at rest based on one or more physiological parameters and measuring a basal/resting heart rate of the patient in response to a determination that the patient is at rest. The method may further include wherein the plurality of threshold heart rates are defined based on the measured basal/resting heart rate.

The method may further include wherein captured arrhythmic ECG segments are reviewable at a remote monitoring center, wherein the captured arrhythmic ECG segments includes one or more tags that can be utilized to filter and search the plurality of captured arrhythmic ECG segments.

The method may further include wherein the tags include one or more of a heart-rate threshold that triggered capture of the ECG segment, a rate-based sensitivity level associated with the heart-rate threshold, ratio of beats exceeding the heart-rate threshold, trigger arrhythmic condition, and patient activity level.

In another embodiment, a system for monitoring electrocardiogram (ECG) signals and detecting arrhythmic ECG episodes may include a monitoring device having one or more electrodes and sensing circuitry for monitoring ECG signals associated with a patient and a processing module configured to receive the monitored ECG, wherein the processing module utilizes a plurality of heart-rate thresholds and rate-dependent sensitivity levels to detect and capture arrhythmic ECG segments.

The system of the preceding paragraph can optionally include, additionally and/or alternatively any, one or more of the following features, configurations and/or additional components.

The processing module of the system may be included on the monitoring device and may further include memory for storing the plurality of heart-rate thresholds and rate-dependent sensitivity levels and a processor for processing the monitored ECG signals using the heart-rate thresholds and rate-dependent sensitivity levels.

The processing module of the system may further include wireless communications circuitry for communicating captured ECG segments to a remote monitoring center for review.

The system may further include wherein the plurality of threshold heart rates include a plurality of heart rate thresholds associated with tachycardia thresholds and a plurality of heart rate thresholds associated with bradycardia thresholds, and wherein higher rate tachycardia thresholds are assigned a higher sensitivity level than lower rate tachycardia thresholds, and lower rate bradycardia thresholds are assigned a higher sensitivity level than higher rate bradycardia thresholds.

The system may further include wherein the plurality of heart rate thresholds are selected based on one or more patient characteristics, comprising one or more of patient age, weight, sex, and/or basal/resting heart rate.

The system may further include wherein the processing module determines whether the patient is at rest based on one or more physiological parameters measures a basal/resting heart rate of the patient in response to a determination that the patient is at rest, wherein the plurality of threshold heart rates are defined based on the measured basal/resting heart rate.

The system may further include wherein the captured arrhythmic ECG segments communicated to a remote monitoring center include one or more tags that can be utilized to filter and search the plurality of captured arrhythmic ECG segments, wherein tags comprise one or more of a heart-rate threshold that triggered capture of the ECG segment, a rate-based sensitivity level associated with the heart-rate threshold, ratio of beats exceeding the heart-rate threshold, trigger arrhythmic condition, and patient activity level.

In another embodiment, a medical includes a sensing unit, a memory unit, and a processor. The sensing unit is configured to monitor an electrocardiogram (ECG) signal. The memory unit is configured to store a plurality of heart-rate thresholds and rate-dependent sensitivity levels, and the processor is configured to process the monitored ECG signal to detect and capture arrhythmic ECG segments based on the plurality of heart-rate thresholds and rate-dependent sensitivity levels.

The medical device of the preceding paragraph can optionally include, additionally and/or alternatively any, one or more of the following features, configurations and/or additional components.

The medical device may further include wherein the processing module determines whether the patient is at rest based on one or more physiological parameters measures a basal/resting heart rate of the patient in response to a determination that the patient is at rest, wherein the plurality of threshold heart rates are defined based on the measured basal/resting heart rate.

The medical device may further include wherein the plurality of threshold heart rates include a plurality of heart rate thresholds associated with tachycardia thresholds and a plurality of heart rate thresholds associated with bradycardia thresholds, and wherein higher rate tachycardia thresholds are assigned a higher sensitivity level than lower rate tachycardia thresholds, and lower rate bradycardia thresholds are assigned a higher sensitivity level than higher rate bradycardia thresholds The medical device may further include wherein the medical device is one of an adherent device, an implantable device, an insertable device, an injectable device or a wearable device.

What is claimed is:

1. A method of detecting arrhythmic electrocardiogram (ECG) signals, the method comprising:
    monitoring one or more physiological parameters associated with a patient;
    determining whether the patient is at rest based on one or more physiological parameters; and
    measuring a basal/resting heart rate of the patient in response to a determination that the patient is at rest, wherein the plurality of threshold heart rates are defined based on the measured basal/resting heart rate;
    defining a plurality of threshold heart rates and rate-dependent sensitivity levels for detecting arrhythmic ECG episodes, wherein the plurality of threshold heart rates are defined based on the measured basal/resting heart rate, wherein more clinically relevant heart rates are assigned rate-dependent sensitivity levels with higher sensitivities;
    monitoring ECG signals associated with a patient using a monitoring device; and
    processing the monitored ECG signals using the plurality of threshold heart rates and rate-dependent sensitivity levels to detect and capture arrhythmic ECG segments.

2. The method of claim 1, wherein the monitoring device processes the monitored ECG signals locally, and wherein captured arrhythmic ECG segments are communicated to a remote monitoring center for review.

3. The method of claim 1, wherein monitored ECG signals are communicated to a remote monitoring center for processing of the monitored ECG signals using the plurality of threshold heart rates and rate-dependent sensitivity levels.

4. The method of claim 1, wherein the plurality of threshold heart rates include a plurality of heart rate thresholds associated with tachycardia thresholds and a plurality of heart rate thresholds associated with bradycardia thresholds, and wherein higher rate tachycardia thresholds are assigned a higher sensitivity level than lower rate tachycardia thresholds, and lower rate bradycardia thresholds are assigned a higher sensitivity level than higher rate bradycardia thresholds.

5. The method of claim 1, wherein the plurality of heart rate thresholds are selected based on one or more patient characteristics.

6. The method of claim 5, wherein the one or more patient characteristics include one or more of patient age, weight, sex, and/or basal/resting heart rate.

7. The method of claim 1, wherein captured arrhythmic ECG segments are reviewable at a remote monitoring center, wherein the captured arrhythmic ECG segments includes one or more tags that can be utilized to filter and search the plurality of captured arrhythmic ECG segments.

8. The method of claim 7, wherein the tags include one or more of a heart-rate threshold that triggered capture of the ECG segment, a rate-based sensitivity level associated with the heart-rate threshold, ratio of beats exceeding the heart-rate threshold, trigger arrhythmic condition, and patient activity level.

9. A system for monitoring electrocardiogram (ECG) signals and detecting arrhythmic ECG episodes, the system comprising:
    a monitoring device having one or more electrodes and sensing circuitry for monitoring ECG signals associated with a patient; and
    a processing module configured to receive the monitored ECG, wherein the processing module utilizes a plurality of heart-rate thresholds and rate-dependent sensitivity levels to detect and capture arrhythmic ECG segments, wherein the processing module determines whether the patient is at rest based on one or more physiological parameters, and measures a basal/resting heart rate of the patient in response to a determination that the patient is at rest, wherein the plurality of threshold heart rates are defined based on the measured basal/resting heart rate.

10. The system of claim 9, wherein the processing module is included on the monitoring device and includes memory for storing the plurality of heart-rate thresholds and rate-dependent sensitivity levels and a processor for processing the monitored ECG signals using the heart-rate thresholds and rate-dependent sensitivity levels.

11. The system of claim 10, wherein the processing module includes wireless communications circuitry for communicating captured ECG segments to a remote monitoring center for review.

12. The system of claim 9, wherein the plurality of threshold heart rates include a plurality of heart rate thresholds associated with tachycardia thresholds and a plurality of heart rate thresholds associated with bradycardia thresholds, and wherein higher rate tachycardia thresholds are assigned a higher sensitivity level than lower rate tachycardia thresholds, and lower rate bradycardia thresholds are assigned a higher sensitivity level than higher rate bradycardia thresholds.

13. The system of claim 9, wherein the plurality of heart rate thresholds are selected based on one or more patient characteristics, comprising one or more of patient age, weight, sex, and/or basal/resting heart rate.

14. The system of claim 9, wherein the captured arrhythmic ECG segments communicated to a remote monitoring center include one or more tags that can be utilized to filter and search the plurality of captured arrhythmic ECG segments, wherein tags comprise one or more of a heart-rate threshold that triggered capture of the ECG segment, a rate-based sensitivity level associated with the heart-rate threshold, ratio of beats exceeding the heart-rate threshold, trigger arrhythmic condition, and patient activity level.

15. A medical device, comprising:
- a sensing unit that monitors an electrocardiogram (ECG) signal;
- a memory unit that stores a plurality of heart-rate thresholds and rate-dependent sensitivity levels; and
- a processor that processes the monitored ECG signal to detect and capture arrhythmic ECG segments based on the plurality of heart-rate thresholds and rate-dependent sensitivity levels, wherein the processing module determines whether the patient is at rest based on one or more physiological parameters, and measures a basal/resting heart rate of the patient in response to a determination that the patient is at rest, wherein the plurality of threshold heart rates are defined based on the measured basal/resting heart rate.

16. The medical device of claim 15, wherein the plurality of threshold heart rates include a plurality of heart rate thresholds associated with tachycardia thresholds and a plurality of heart rate thresholds associated with bradycardia thresholds, and wherein higher rate tachycardia thresholds are assigned a higher sensitivity level than lower rate tachycardia thresholds, and lower rate bradycardia thresholds are assigned a higher sensitivity level than higher rate bradycardia thresholds.

17. The medical device of claim 15, wherein the medical device is one of an adherent device, an implantable device, an insertable device, an injectable device or a wearable device.

* * * * *